United States Patent

Honda

[11] Patent Number: 5,637,293
[45] Date of Patent: Jun. 10, 1997

[54] PREPARATION FOR EPIDERMIS

[75] Inventor: Shinsuke Honda, Onojo, Japan

[73] Assignee: Sansho Seiyaku Co., Ltd., Onojo, Japan

[21] Appl. No.: 238,660

[22] Filed: May 5, 1994

[30] Foreign Application Priority Data

Oct. 28, 1993 [JP] Japan ................. 5-270970

[51] Int. Cl.⁶ ................. A61K 7/42; A61K 9/10
[52] U.S. Cl. ................. 424/62; 424/59; 424/401; 424/78.02; 514/938; 514/944
[58] Field of Search ................. 424/45, 62, 401, 424/78.02, 59; 514/938, 944

[56] References Cited

U.S. PATENT DOCUMENTS 4,696,813  9/1987  Higa ......................... 424/62
4,990,330  2/1991  Oyama ...................... 424/62
5,279,834  1/1994  Meybeck .................. 424/450

*Primary Examiner*—Raj Bawa
*Attorney, Agent, or Firm*—Armstrong, Westerman, Hattori, McLeland & Naughton

[57] ABSTRACT

A preparation for epidermis containing kojic acid and/or its derivative and an ultraviolet light absorbent, which has improved preparation stability and which shows lasting effectiveness, is provided. The improved preparation stability is imparted by adding to the preparation at least one member selected from the group consisting of fatty acid esters and fatty acid glycerides.

1 Claim, No Drawings

PREPARATION FOR EPIDERMIS

BACKGROUND OF THE INVENTION

This invention relates to a preparation for epidermis containing kojic acid and/or its derivative and an ultraviolet light absorbent, which further contains at least one member selected from the group consisting of fatty acid esters and fatty acid glycerides for improving stability and attaining lasting effectiveness of the kojic acid and/or its derivative.

As typical forms of preparation for epidermis, there are illustrated O/W (oil-in-water) emulsions and W/O (water-in-oil) emulsions, which are different from each other in water-to-oil composition ratio and physical properties but are both homogeneous preparations wherein oil phase or aqueous phase are stably emulsified and dispersed with the aid of a surfactant.

Kojic acid and its derivatives the inventor has long studied are known as useful agents having various excellent properties, as disclosed in Japanese Unexamined Patent Publication No. 55-157509, Japanese Examined Patent Publication No. S56-18569, S58-22151, S58-22152, S58-34446, S60-7961, S60-9722 and S60-10005, Japanese Unexamined Patent Publication No. S60-137253, Japanese Examined Patent Publication No. S61-10447 and S61-60801, Japanese Unexamined Patent Publication No. S62-5909, Japanese Examined Patent Publication No. S62-3820 and S63-27322, Japanese Unexamined Patent Publication No. H1-132502 and Japanese Examined Patent Publication No. H5-30422.

However, kojic acid and its derivatives (hereinafter these being in some cases merely referred to as "kojic acids") are also known as agents which themselves have difficulty in acquiring stability. Particularly when the kojic acids are incorporated in the aforementioned O/W emulsion or W/O emulsion, it requires a highly sophisticated technique to design a proper formulation. Hence, it has been a pressing subject with respect to formation of a preparation containing the kojic acids to develop a technique which provides the kojic acids-containing prepatation with enough stability to stand severe distributive machinery without giving unpleasant feeling upon application thereof to skin.

In the case of compounding the kojic acids in various preparations for epidermis, they are under the condition of being likely to be exposed to ultraviolet light to varying degrees which can be an external cause of their coloration or decomposition. Thus, it has been conducted to compound an ultraviolet light absorbent in a proper amount for depressing damages by irradiation with ultraviolet light.

Examples thereof are illustrated in, for example, Japanese Unexamined Patent Publication No. S62-108804 and S64-83008 and Japanese Examined Patent Publication No. H4-46924.

Many of such ultraviolet light absorbents have a problem with solubility and separate out in the preparation, and fail to fully exhibit their ultraviolet light-absorbing ability, leading to a deteriorated stability of kojic acid.

In order to overcome this defect, solubilizing agents have properly been used. However, the use of oily solubilizing agent in a large amount causes a problem of giving an unpleasant feeling such as sticking feeling upon application to skin.

In addition, nonionic surfactants, which are properly used as surfactants upon forming a preparation containing kojic acids for external application in view of depressing coloration, giving a pleasant feeling upon application and being harmless to skin, have weaker emulsifying power in comparison with ionic surfactants and suffer decrease in emulsifying power in the presence of a highly polar ingredient or by the influence of pH level. Therefore, in the kojic acid-containing preparation which is usually adjusted to 4 to 5 in pH, incorporation of a highly polar ultraviolet light absorbent causes the problem of deteriorating emulsion stability with time.

SUMMARY OF THE INVENTION

It is, therefore, an object of the present invention to provide a preparation for epidermis which solves the above-described problems with the conventional kojic acid-containing preparation, i.e., which does not suffer separation of the ultraviolet light absorbent and has improved stability with time to coloration and decomposition of kojic acid and has an improved lasting effectiveness of the ingredient, and which is formed by adding at least one member selected from the group consisting of fatty acid esters and fatty acid glycerides.

Other objects, features and advantages of the present invention will become apparent from the detailed description of the preferred embodiments of the invention to follow.

DETAILED DESCRIPTION OF THE PREFERRED EMBODIMENTS OF THE INVENTION

As the kojic acid (5-hydroxy-2-hydroxymethyl-δ-pyrrone) to be used in the present invention as a first ingredient, a pure product of 5-hydroxy-2-hydroxymethyl-δ-pyrrone, a fermentaion liquor containing kojic acid as a major component and being obtained by cultivating a known bacterium strain capable of yielding kojic acid, a concentrate of the fermentation liquor, a product obtained by extracting kojic acid from the fermentation liquor and crystallizing the extract, and the like.

As the kojic acid derivatives, those which are disclosed in, for example, Japanese Examined Patent Publication No. S60-10005, H1-45472 and H3-74229, and esterified products of kojic acid and kojic acid derivatives wherein sugars are bound to the —$CH_2OH$ group at 2-position of kojic acid disclosed in, for example, Japanese Examined Patent Publication No. S58-22151 and S58-22152 may be used alone or in combination of two or more.

The kojic acid and/or its derivative is compounded in the preparation in an amount of 0.001 to 10% by weight, preferably 0.1 to 5% by weight, based on the total amount of the preparation for external application.

The ultraviolet light absorbents to be used in the present invention as a second ingredient are not particularly limited. Preferred examples thereof include benzophenone derivatives such as oxybenzone, oxybenzonesulfonic acid, sodium hydroxymethoxybenzophenonesulfonate and dihydroxy-dimethoxybenzophenone; salicylic acid derivatives such as ethylene glycol salicylate, homomenthyl salicylate and phenyl salicylate; urocanic acid and ethyl urocanate; cinnamic acid derivatives such as 2-ethylhexyl p-methoxycinnamate and octyl methoxycinnamate; p-aminobenzoic acid derivatives such as glyceryl p-aminobenzoate and 2-ethylhexyl p-dimethylaminobenzoate; dibenzoylmethane derivatives such as 4-tert-butyl-4'-methoxydibenzoylmethane; and benzotriazole derivatives such as 2-(2-hydroxy-5-methylphenyl)benzotriazole. These compounds may be used alone or in combination of two or more. In addition, other known animal or vegetable extracts having ultraviolet light-absorbing ability may properly be used alone or in combination.

Amounts of these ultraviolet light absorbents are somewhat varied depending upon the kind thereof but, usually, they are used in an amount of 0.001 to 10% by weight, preferably 0.1 to 5% by weight, based on the total amount of the preparation for external application.

As the fatty acid esters to be used in the present invention as a third ingredient, there are illustrated higher alcohol fatty acid esters such as isopropyl adipate, avocado oil fatty acid ethyl ester, isocetyl isostearate, isopropyl isostearate, isodecyl isononanoate, octyl isopalmitate, octyl isopelargonate, octyldodecyl erucate, octyl hydroxystearate, octyldodecyl oleate, oleyl oleate, decyl oleate, dioctyl succinate, hexyldecyl dimethyloctanoate, isocetyl stearate, butyl stearate, octyldodecyl lactate, oleyl lactate, cetyl lactate, myristyl lactate, lauryl lactate, isostearyl palmitate, isopropyl palmitate, octyl palmitate, cetyl palmitate, castor oil fatty acid methyl ester, diethyl phthalate, eicosanyl propionate, stearyl heptanoate, isostearyl myristate, isocetyl myristate, isotridecyl myristate, isopropyl myristate, octyldodecyl myristate, cetyl myristate, decyl myristate, butyl myristate, myristyl myristate, hexyl laurate, octyldodecyl ricinoleate, cetyl ricinoleate, isopropyl linolate and diisostearyl malate; ethylene glycol fatty acid esters such as ethylene glycol fatty acid ester, ethylene glycol dioctanoate, ethylene glycol dioleate, ethylene glycol distearate and ethylene glycol monostearate; polyethylene glycol fatty acid esters such as diethylene glycol laurate, diethylene glycol dilaurate, polyoxyl 40 stearate, polyethylene glycol palmitate, polyoxyethylene coconut oil fatty acid ester (6E.O.), polyethylene glycol myristate, polyethylene glycol monooleate and polyethylene glycol monolaurate; propylene glycol fatty acid esters such as propylene glycol fatty acid ester, self-emulsifiable propylene glycol stearate, propylene glycol monostearate, propylene glycol dioleate, propylene glycol dicaprylate and propylene glycol dicaprylate; glycol fatty acid esters such as neopentylglycol dioctanoate, neopentylglycol dicaprylate, butanediol dimontanate and alkylene (18, 20) straight chain glycol monoisostearate; trimethylolpropane fatty acid esters such as trimethylolpropane triisostearate and trimethylolpropane trioctanoate; pentaerythritol fatty acid esters such as pentaerythritol fatty acid (1), pentaerythritol tetraoctanoate and pentaerythritol tetramyristate; sorbitol fatty acid esters such as sorbitol sesquiisostearate, sorbitol sesquioleate, sorbitol trioleate and sorbitol coconut oil fatty acid ester; polyoxyethylene sorbitol fatty acid esters such as polyoxyethylene sorbitol (20E.O.) isostearate, polyoxyethylene sorbitol (20E.O.) trioleate, polyoxyethylene sorbitol (20E.O.) tristearate, polyoxyethylene sorbitol hexastearate, polyoxyethylene sorbitol bees wax, polyoxyethylene coconut oil fatty acid sorbitol ester (20E.O.) and polyoxyethylene sorbitol (6E.O.) monooleate; and sugar fatty acid esters such as sucrose benzoate, sucrose acetate isobutyrate, sucrose stearate and sucrose ester of coconut oil fatty acid and, as the fatty acid glycerides, there are illustrated glycerol fatty acid esters such as glyceryl arachate, glyceryl isostearate, glyceryl oleate (1), wheat germ oil fatty acid glyceride, mixed fatty acid triglyceride, isopalmitic acid diglyceride, hydrogenated soybean oil fatty acid diglyceride, myristic acid diglyceride, cotton seed fatty acid diglyceride, coconut oil fatty acid diglyceride, hydrogenated soybean oil fatty acid diglyceride, glyceryl stearate malate, sesquioleic acid glyceride, capric and caprylic acid triglyceride, tallow fatty acid triglyceride, myristic acid triglyceride, coconut oil fatty acid triglyceride, saturated fatty acid triglyceride and saturated fatty acid glyceride (2), polyglycerol fatty acid esters such as diglyceryl isostearate, diglyceryl oleate, diglyceryl stearate, diglyceryl diisostearate, tetraglyceryl oleate, tetraglyceryl laurate, hexaglyceryl oleate, hexaglyceryl laurate, decaglyceryl laurate, decaglyceryl diisostearate and decaglyceryl decaoleate; and polyoxyethylene glycerol fatty acid esters such as polyoxyethylene glyceryl isostearate, polyoxyethylene glyceryl triisostearate, polyoxyethylene glyceryl oleate and polyoxyethylene glyceryl monostearate. Of these, middle-chain fatty acid (containing 6 to 12 carbon atoms) monoglycerides, diglycerides and triglycerides are most preferred. These compounds may be used alone or in combination of two or more.

Amounts of the third ingredient somewhat varies depending upon the kind thereof but, usually, they are addded in an amount of 0.001 to 20% by weight, preferably 0.1 to 10% by weight, based on the total amount of the preparation.

The above-described first to three ingredients may be formed into a preparation for external application in a known manner. Such preparation does not suffer separation of the ultraviolet light absorbent, thus being a stable emulsion preparation having good stability with time, in which the kojic acids show improved stability to coloration and decomposition with time and exhibit lasting effectiveness.

Needless to say, form of the preparation of the present invention is not limited to the emulsion type such as O/W emulsion and W/O emulsion, but may be a transparent type by properly selecting the ingredients. In addition, the present invention may also be applicable as a fundamental technique for forming multi-layer emulsion preparations such as W/O/W or O/W/O emulsions or microcapsule preparations.

The preparation of the present invention for epidermis is not particularly limited as to application form, and may be widely used in a known application form of medicines, quasi-drugs and cosmetics such as cataplasm, plaster, paste, cream, ointment, aerosol, emulsion, lotion, essence, pack, gel, powder, foundation, suncare, bath salts, and the like.

In forming the preparation of the present invention, various known and conventionally used effective ingredients may optionally be incorporated as the case demands in amounts not spoiling the objects of the present invention. Examples of such known effective ingredients include capillary vasodilators such as carpronium chloride, cepharanthine, vitamin E, vitamin E nicotinate, nicotinic acid, nicotinic acid amide, benzyl nicotinate, ginger tincture and chili tincture; coolers such as camphor, mentol and peppermint oil; antimicrobial agents such as hinokitiol, benzalkonium chloride and undecylenic acid; anti-inflammatory agents such as adrenal cortical hormone, -aminocaproic acid, lysozyme chloride, glycyrrhizin and allantoin; fairness-imparting agents such as ascorbic acid and arbutin; various extracts of animal or vegetable origin such as placenta extract, liver extract, lithospermum root extract and extract of culture liquor of lactic acid bacteria.

In addition to the known effective ingredients, various known additives such as humectants, antiseptics, antioxidants, chelating agents, pH-adjusting agents, perfumes and colorants may also be used, as well as a base ingredient such as a fat and oil, within a range of not spiling the objects of the present invention in the above-described application forms of medicines, quasi-drugs and cosmetics.

The present invention is now described in more detail by reference to experiments and formulations which, however, are not construed to be limitative at all.

Experiment 1

Preparation stability test

Method of experiment:

Various creams (pH: about 4.5) were prepared according to the formulations shown in Table 1. After placing them in 4-ounce candle bottle, they were stored for 2 months under the severe condition of 50° C. while irradiating with ultraviolet light. After 2 months, color difference (ΔE) was measured (using a color-difference meter, Z-1001DP, made by Nihon Denshoku Kogyo). In this occasion, observation of change in appearance (separation of the ultraviolet light absorbent and stability of the emulsion) and evaluation of application feeling were also conducted.

Results of the experiment

As is shown in Table 1, the preparations in accordance with the present invention containing ingredients 1 to 8 suffered no separation of the ultraviolet light absorbent and showed an extremely good emulsion stability. Coloration of kojic acid contained in the preparations was not observed, and application feeling was kept good.

TABLE 1

Tested Samples and Experiment Results

| Name of Ingredient | | Examples | | | | | | | |
|---|---|---|---|---|---|---|---|---|---|
| | | 1 | 2 | 3 | 4 | 5 | 6 | 7 | 8 |
| 1. Myristic acid triglyceride | | 5.00 | 5.00 | 2.00 | — | — | — | — | — |
| 2. Myristyl lactate | | — | 2.00 | — | — | — | — | 2.00 | — |
| 3. Propylene glycol dioleate | | — | — | 5.00 | — | 0.50 | — | — | — |
| 4. Diglyceryl diisostearate | | — | — | — | 0.50 | — | — | — | — |
| 5. Pentaerythritol tetramyristate | | — | — | — | — | 1.50 | — | — | — |
| 6. Sorbitol sesquiisostearate | | — | — | — | — | — | 0.50 | — | — |
| 7. Polyoxyethylene sorbitol (20 E.O.) tristearate | | — | — | — | — | — | — | 1.50 | — |
| 8. Hydrogenated soybean oil fatty acid glyceride | | — | — | — | — | — | — | — | 3.00 |
| 9. Kojic acid | | 1.00 | 1.00 | 1.00 | 1.00 | 1.00 | 1.00 | 1.00 | 1.00 |
| 10. Oxybenzone | | 1.50 | — | 0.80 | — | — | — | — | — |
| 11. 4-tert-Butyl-4'-methoxy-dibenzoyl-methane | | — | 1.00 | 0.50 | — | — | — | 0.20 | — |
| 12. Glyceryl p-aminobenzoate | | — | — | — | 0.20 | — | — | 0.10 | 1.50 |
| 13. Ethylene glycol salicylate | | — | — | — | — | 1.00 | — | — | — |
| 14. Octyl methoxycinnamate | | — | — | — | — | — | 0.50 | — | 0.10 |
| 15. Bees wax | | 4.50 | 4.50. | 4.50 | 4.50 | 4.50 | 4.50 | 4.50 | 4.50 |
| 16. Vaseline | | 2.80 | 2.80 | 2.80 | 2.80 | 2.80 | 2.80 | 2.80 | 2.80 |
| 17. Jojoba oil | | 7.00 | 7.00 | 7.00 | 7.00 | 7.00 | 7.00 | 7.00 | 7.00 |
| 18. Natural vitamin E | | 0.04 | 0.04 | 0.04 | 0.04 | 0.04 | 0.04 | 0.04 | 0.04 |
| 19. Polyoxyethylene cetyl ether (25 E.O.) | | 1.50 | 1.50 | 1.50 | 1.50 | 1.50 | 1.50 | 1.50 | 1.50 |
| 20. Polyoxyethylene stearyl ether (20 E.O.) | | 0.70 | 0.70 | 0.70 | 0.70 | 0.70 | 0.70 | 0.70 | 0.70 |
| 21. Carboxyvinyl polymer | | 0.08 | 0.08 | 0.08 | 0.08 | 0.08 | 0.08 | 0.08 | 0.08 |
| 22. Sodium dl-Pyrrolidone carboxylate | | 6.00 | 6.00 | 6.00 | 6.00 | 6.00 | 6.00 | 6.00 | 6.00 |
| 23. Disodium edetate | | 0.02 | 0.02 | 0.02 | 0.02 | 0.02 | 0.02 | 0.02 | 0.02 |
| 24. Citric acid | | *1 | *1 | *1 | *1 | *1 | *1 | *1 | *1 |
| 25. Sodium citrate | | *1 | *1 | *1 | *1 | *1 | *1 | *1 | *1 |
| 26. Purified water | | *2 | *2 | *2 | *2 | *2 | *2 | *2 | *2 |
| Resilts of the tests | Appearance *3 | no | no | no | no | no | no | no | no |
| | *4 | ⊚ | ⊚ | ⊚ | ⊚ | ⊚ | ⊚ | ⊚ | ⊚ |
| | Color difference (ΔE) | 3.4 | 3.0 | 2.9 | 2.5 | 2.8 | 3.1 | 2.0 | 2.7 |
| | Evaluation of feeling upon application (*5) *6 *7 *8 | ⊚ ⊚ ⊚ | ⊚ ⊚ ⊚ | ⊚ ⊚ ⊚ | ⊚ ⊚ ⊚ | ⊚ ⊚ ⊚ | ⊚ ⊚ ⊚ | ⊚ ⊚ ⊚ | ⊚ ⊚ ⊚ |

| Name of Ingredient | Comparative Examples | | | | | | | | |
|---|---|---|---|---|---|---|---|---|---|
| | 1 | 2 | 3 | 4 | 5 | 6 | 7 | 8 | 9 |
| 1. Glyceryl trimyristate | — | — | — | — | — | — | — | — | — |
| 2. Myristyl lactate | — | — | — | — | — | — | — | — | — |
| 3. Propylene glycol dioleate | — | — | — | — | — | — | — | — | — |
| 4. Diglyceryl diisostearate | — | — | — | — | — | — | — | — | — |

TABLE 1-continued

Tested Samples and Experiment Results

| | | | | | | | | | | |
|---|---|---|---|---|---|---|---|---|---|---|
| 5. Pentaerythritol tetramyristate | | — | — | — | — | — | — | — | — | — |
| 6. Sorbitol sesqui-isostearate | | — | — | — | — | — | — | — | — | — |
| 7. Polyoxyethylene sorbitol (20 E.O.), tristearate | | — | — | — | — | — | — | — | — | — |
| 8. Hydrogenated soybean oil fatty acid glyceride | | — | — | — | — | — | — | — | — | — |
| 9. Kojic acid | | 1.00 | 1.00 | 1.00 | 1.00 | 1.00 | 1.00 | 1.00 | 1.00 | 1.00 |
| 10. Oxybenzone | | — | 1.50 | — | 0.80 | — | — | — | — | — |
| 11. 4-tert-Butyl-4'-methoxy-dibenzoyl-methane | | — | — | 1.00 | 0.50 | — | — | — | 0.20 | — |
| 12. Glyceryl p-amino-benzoate | | — | — | — | — | 0.20 | — | — | 0.10 | 1.50 |
| 13. Ethylene glycol salicylate | | — | — | — | — | — | 1.00 | — | — | — |
| 14. Octyl methoxycinnamate | | — | — | — | — | — | — | 0.50 | — | 0.10 |
| 15. Bees wax | | 4.50 | 4.50 | 4.50 | 4.50 | 4.50 | 4.50 | 4.50 | 4.50 | 4.50 |
| 16. Vaseline | | 2.80 | 2.80 | 2.80 | 2.80 | 2.80 | 2.80 | 2.80 | 2.80 | 2.80 |
| 17. Jojoba oil | | 7.00 | 7.00 | 7.00 | 7.00 | 7.00 | 7.00 | 7.00 | 7.00 | 7.00 |
| 18. Natural vitamin E | | 0.04 | 0.04 | 0.04 | 0.04 | 0.04 | 0.04 | 0.04 | 0.04 | 0.04 |
| 19. Polyoxyethylene cetyl ether(25 E.O.) | | 1.50 | 1.50 | 1.50 | 1.50 | 1.50 | 1.50 | 1.50 | 1.50 | 1.50 |
| 20. Polyoxyethylene stearyl ether (20 E.O.) | | 0.70 | 0.70 | 0.70 | 0.70 | 0.70 | 0.70 | 0.70 | 0.70 | 0.70 |
| 21. Carboxyvinyl polymer | | 0.08 | 0.08 | 0.08 | 0.08 | 0.08 | 0.08 | 0.08 | 0.08 | 0.08 |
| 22. Soln. of sodium dl-pyrrolidone carboxylate | | 6.00 | 6.00 | 6.00 | 6.00 | 6.00 | 6.00 | 6.00 | 6.00 | 6.00 |
| 23. Disodium edetate | | 0.02 | 0.02 | 0.02 | 0.02 | 0.02 | 0.02 | 0.02 | 0.02 | 0.02 |
| 24. Citric acid | | *1 | *1 | *1 | *1 | *1 | *1 | *1 | *1 | *1 |
| 25. Sodium citrate | | *1 | *1 | *1 | *1 | *1 | *1 | *1 | *1 | *1 |
| 26. Purified water | | *2 | *2 | *2 | *2 | *2 | *2 | *2 | *2 | *2 |
| Results of the tests | Appearance *3 | — | no | yes | yes | yes | yes | yes | yes | yes |
| | *4 | Δ | X | X | X | X | X | X | X | X |
| | Color difference (ΔE) | 9.1 | 8.5 | 7.7 | 7.9 | 10.3 | 7.2 | 8.6 | 8.1 | 6.5 |
| | Evaluation *6 | ◉ | ◉ | ◉ | X | X | X | X | X | X |
| | of feeling *7 | Δ | X | X | Δ | Δ | Δ | Δ | X | X |
| | upon application (*5) *8 | Δ | Δ | X | Δ | X | Δ | X | X | Δ |

*1: slight amount
*2: enough amount to make the total amount 100% by weight
*3: Separation of ultraviolet light absorbent
*4: Emulsion state (no separation)
  ◉: good; Δ: partly separated; X: separated
*5: Standard of evaluation:
  ◉: good; O: almost no problem; Δ: slight problem; X: bad
*6: rough feel
*7: sticky feel
*8: fitness to skin Experiment 2

Effect of depressing pigmentation of guinea pig induced by UV light

Effect of depressing pigmentation was examined using yellowish brown guinea pigs.

Results of the experiment are tabulated in Table 2.

As can be seen from the results in Table 2, the preparations of the present invention show excellent and lasting pigmentation-depressing effect.

Method of experiment

Back fur of yellowish guinea pigs was clipped off to lay bare the back skin thereof, and the bare back skin was shaved with an electric razor. Each of the shaved backs was covered with a piece of aluminum foil having four square holes (2.0×2.0 cm), and was irradiated with UV-B (having 3 SE lamps; 140 mJ/cm$^2$) for 90 seconds a day four times every three days. Each of the preparations obtained in Experiment 1 was applied to the irradiated test site from the initiation of the irradiation three times a day for 20 consecutive days. Concentration of the ingredient in the mustle tissue was measured and pigmentation was scored between 13th day and 20th day after initiation of UV light irradiation.

Blackened degree of tested skin was scored with the naked eye according to the following standard.

Scoring standard:
  3: No pigmentation was observed.
  2: Slight pigmentation was observed.
  1: Middle degree pigmentation was observed.
  0: Pigmentation was observed to the same degree as on control site (non-treated).
  −1: Pigmentation was observed to a stronger degree than on control site (non-treated).

Results of the experiments

The preparations of the present invention were confirmed to immediately show excellent pigmentation-depressing effect.

TABLE 2

Results of experiments

| Name of Ingredient | Examples | | | | | | | |
|---|---|---|---|---|---|---|---|---|
| | 1 | 2 | 3 | 4 | 5 | 6 | 7 | 8 |
| 1. Myristic acid triglyceride | 5.00 | 5.00 | 2.00 | — | — | — | — | — |
| 2. Myristyl lactate | — | 2.00 | — | — | — | — | 2.00 | — |
| 3. Propylene glycol dioleate | — | — | 5.00 | — | 0.50 | — | — | — |
| 4. Diglyceryl diisostearate | — | — | — | 0.50 | — | — | — | — |
| 5. Pentaerythritol tetramyristate | — | — | — | — | 1.50 | — | — | — |
| 6. Sorbitol sesquiisostearate | — | — | — | — | — | 0.50 | — | — |
| 7. Polyoxyethylene sorbitol (20 E.O.) tristearate | — | — | — | — | — | — | 1.50 | — |
| 8. Hydrogenated soybean oil fatty acid glyceride | — | — | — | — | — | — | — | 3.00 |
| 9. Kojic acid | 1.00 | 1.00 | 1.00 | 1.00 | 1.00 | 1.00 | 1.00 | 1.00 |
| 10. Oxybenzone | 1.50 | — | 0.80 | — | — | — | — | — |
| 11. 4-tert-Butyl-4'-methoxy-dibenzoyl-methane | — | 1.00 | 0.50 | — | — | — | 0.20 | — |
| 12. Glyceryl p-aminobenzoate | — | — | — | 0.20 | — | — | 0.10 | 1.50 |
| 13. Ethylene glycol salicylate | — | — | — | — | 1.00 | — | — | — |
| 14. Octyl methoxycinnamate | — | — | — | — | — | 0.50 | — | 0.10 |
| 15. Bees wax | 4.50 | 4.50 | 4.50 | 4.50 | 4.50 | 4.50 | 4.50 | 4.50 |
| 16. Vaseline | 2.80 | 2.80 | 2.80 | 2.80 | 2.80 | 2.80 | 2.80 | 2.80 |
| 17. Jojoba oil | 7.00 | 7.00 | 7.00 | 7.00 | 7.00 | 7.00 | 7.00 | 7.00 |
| 18. Natural vitamin E | 0.04 | 0.04 | 0.04 | 0.04 | 0.04 | 0.04 | 0.04 | 0.04 |
| 19. Polyoxyethylene cetyl ether(25 E.O.) | 1.50 | 1.50 | 1.50 | 1.50 | 1.50 | 1.50 | 1.50 | 1.50 |
| 20. Polyoxyethylene stearyl ether (20 E.O.) | 0.70 | 0.70 | 0.70 | 0.70 | 0.70 | 0.70 | 0.70 | 0.70 |
| 21. Carboxyvinyl polymer | 0.08 | 0.08 | 0.08 | 0.08 | 0.08 | 0.08 | 0.08 | 0.08 |
| 22. Soln. of sodium dl-pyrrolidone carboxylate | 6.00 | 6.00 | 6.00 | 6.00 | 6.00 | 6.00 | 6.00 | 6.00 |
| 23. Disodium edetate | 0.02 | 0.02 | 0.02 | 0.02 | 0.02 | 0.02 | 0.02 | 0.02 |
| 24. Citric acid | *1 | *1 | *1 | *1 | *1 | *1 | *1 | *1 |
| 25. Sodium citrate | *1 | *1 | *1 | *1 | *1 | *1 | *1 | *1 |
| 26. Purified water | *2 | *2 | *2 | *2 | *2 | *2 | *2 | *2 |
| Scoring of the effect — Concentration of kojic acid in muscle tissue (µg/g) | 0.5 | 0.4 | 0.4 | 0.7 | 0.4 | 0.6 | 0.5 | 0.4 |
| Degree of pigmentation | 3 | 3 | 3 | 3 | 3 | 3 | 3 | 3 |
| Days necessary for obtaining pigmentation-curing effect (days) | 14 | 15 | 13 | 14 | 15 | 13 | 14 | 15 |

| Name of Ingredient | Comparative Examples | | | | | | | | |
|---|---|---|---|---|---|---|---|---|---|
| | 1 | 2 | 3 | 4 | 5 | 6 | 7 | 8 | 9 |
| 1. Glyceryl trimyristate | — | — | — | — | — | — | — | — | — |
| 2. Myristyl lactate | — | — | — | — | — | — | — | — | — |
| 3. Propylene glycol dioleate | — | — | — | — | — | — | — | — | — |
| 4. Diglyceryl diisostearate | — | — | — | — | — | — | — | — | — |
| 5. Pentaerythritol tetramyristate | — | — | — | — | — | — | — | — | — |
| 6. Sorbitol sesqui- | — | — | — | — | — | — | — | — | — |

TABLE 2-continued

Results of experiments

| | | | | | | | | | |
|---|---|---|---|---|---|---|---|---|---|
| isostearate | | | | | | | | | |
| 7. Polyoxyethylene sorbitol (20 E.O.), tristearate | — | — | — | — | — | — | — | — | — |
| 8. Hydrogenated soybean oil fatty acid glyceride | — | — | — | — | — | — | — | — | — |
| 9. Kojic acid | 1.00 | 1.00 | 1.00 | 1.00 | 1.00 | 1.00 | 1.00 | 1.00 | 1.00 |
| 10. Oxybenzone | — | 1.50 | — | 0.80 | — | — | — | — | — |
| 11. 4-tert-Butyl-4'-methoxy-dibenzoylmethane | — | — | 1.00 | 0.50 | — | — | — | 0.20 | — |
| 12. Glyceryl p-aminobenzoate | — | — | — | — | 0.20 | — | — | 0.10 | 1.50 |
| 13. Ethylene glycol salicylate | — | — | — | — | — | 1.00 | — | — | — |
| 14. Octyl methoxycinnamate | — | — | — | — | — | — | 0.50 | — | 0.10 |
| 15. Bees wax | 4.50 | 4.50 | 4.50 | 4.50 | 4.50 | 4.50 | 4.50 | 4.50 | 4.50 |
| 16. Vaseline | 2.80 | 2.80 | 2.80 | 2.80 | 2.80 | 2.80 | 2.80 | 2.80 | 2.80 |
| 17. Jojoba oil | 7.00 | 7.00 | 7.00 | 7.00 | 7.00 | 7.00 | 7.00 | 7.00 | 7.00 |
| 18. Natural vitamin E | 0.04 | 0.04 | 0.04 | 0.04 | 0.04 | 0.04 | 0.04 | 0.04 | 0.04 |
| 19. Polyoxyethylene cetyl ether (25 E.O.) | 1.50 | 1.50 | 1.50 | 1.50 | 1.50 | 1.50 | 1.50 | 1.50 | 1.50 |
| 20. Polyoxyethylene stearyl ether (20 E.O.) | 0.70 | 0.70 | 0.70 | 0.70 | 0.70 | 0.70 | 0.70 | 0.70 | 0.70 |
| 21. Carboxyvinyl polymer | 0.08 | 0.08 | 0.08 | 0.08 | 0.08 | 0.08 | 0.08 | 0.08 | 0.08 |
| 22. Soln. of sodium dl-pyrrolidone carboxylate | 6.00 | 6.00 | 6.00 | 6.00 | 6.00 | 6.00 | 6.00 | 6.00 | 6.00 |
| 23. Disodium edetate | 0.02 | 0.02 | 0.02 | 0.02 | 0.02 | 0.02 | 0.02 | 0.02 | 0.02 |
| 24. Citric acid | *1 | *1 | *1 | *1 | *1 | *1 | *1 | *1 | *1 |
| 25. Sodium citrate | *1 | *1 | *1 | *1 | *1 | *1 | *1 | *1 | *1 |
| 26. Purified water | *2 | *2 | *2 | *2 | *2 | *2 | *2 | *2 | *2 |
| Scoring of the effect — Concentration of kojic acid in muscle tissue (µg/g) | 0.2 | 0.2 | 0.2 | 0.2 | 0.2 | 0.2 | 0.2 | 0.2 | 0.2 |
| Degree of pigmentation | 1 | 1 | 1 | 1 | 1 | 1 | 1 | 1 | 1 |
| Days necessary for obtaining pigmentation-curing effect (days) | 18 | 19 | 18 | 18 | 19 | 19 | 18 | 19 | 19 |

*1: slight amount
*2: enough amount to make the total amount 100% by weight

Formulation examples of the present invention are shown below.

Formulation example 1 [Cream(1)]

| | (% by weight) |
|---|---|
| 1. Kojic acid | 1.00 |
| 2. Oxybenzonesulfonic acid | 0.50 |
| 3. Diisopropyl adipate | 2.00 |
| 4. Isopropyl myristate | 3.00 |
| 4. Isopropyl myristate | 3.00 |
| 5. Polyoxyethylene cetyl ether (25E.O.) | 5.00 |
| 6. Stearic acid | 5.00 |
| 7. Avocado oil | 1.00 |
| 8. Almond oil | 10.00 |
| 9. Solution of sodium dl-pyrrolidonecarboxylate | 5.00 |
| 10. p-Hydroxybenzoic acid ester | 0.20 |
| 11. Disodium edetate | 0.01 |
| 12. Purified water to make | 100.00 |

Formulation example 2 [Cream(2)]

| | (% by weight) |
|---|---|
| 1. Kojic acid | 5.00 |
| 2. 4-tert-Butyl-4'-methoxy-dibenzoylmethane | 0.50 |
| 3. Octyldodecyl lactate | 1.00 |
| 4. Myristyl lactate | 0.20 |
| 5. Polyoxyethylene lanolin | 3.00 |
| 6. Dimethylsiloxane methyl(polyoxyethylene-polyoxypropylene copolymer) | 3.00 |
| 7. Jojoba oil | 7.00 |
| 8. Decamethylcyclopentasiloxane | 3.00 |
| 9. Octamethylcyclotetrasiloxane | 3.00 |
| 10. Dimethylpolysiloxane | 5.00 |
| 11. Natural vitamin E | 0.04 |
| 12. 1% Solution of sodium hyaluronate | 2.00 |
| 13. Carrageenan | 1.00 |
| 14. Disodium edetate | 0.01 |
| 15. Purified water to make | 100.00 |

Formulation example 3 [Emulsion (1)]

| | (% by weight) |
|---|---|
| 1. Kojic acid | 4.00 |
| 2. 2-Ethylhexyl p-methoxycinnamate | 2.00 |
| 3. Isostearic acid glyceride | 4.00 |
| 4. Stearic acid polyoxyethylene monoglyceride | 2.00 |
| 5. Polyoxyethylene cetyl ether (25E.O.) | 0.50 |
| 6. Polyoxyethylene oleyl ether (20E.O.) | 1.00 |
| 7. Stearic acid | 0.50 |
| 8. Shea butter | 0.50 |
| 9. Avocado oil | 4.00 |
| 10. p-Hydroxybenzoic acid ester | 0.20 |
| 11. Quince seed extract | 5.00 |
| 12. Xanthane gum | 0.14 |
| 13. Disodium edetate | 0.01 |
| 14. Purified water to make | 100.00 |

Formulation example 4 [Emulsion (2)]

| | (% by weight) |
|---|---|
| 1. Kojic acid | 0.50 |
| 2. 2-Ethylene glycol salicylate | 0.10 |
| 3. Octyl methoxycinnamate | 2.00 |
| 4. Coconut oil fatty acid sucrose ester | 0.50 |
| 5. Myristyl myristate | 4.00 |
| 6. Coconut oil fatty acid monoethanolamide | 2.00 |
| 7. Stearic acid | 0.50 |
| 8. Myristic acid | 0.50 |
| 9. Avocado oil | 4.00 |
| 10. Natural vitamin E | 0.04 |
| 11. p-Hydroxybenzoic acid ester | 0.20 |
| 12. Sodium hyaluronate | 5.00 |
| 13. Xanthane gum | 0.14 |
| 14. Disodium edetate | 0.01 |
| 15. Purified water to make | 100.00 |

Formulation example 5 [Lotion]

| | (% by weight) |
|---|---|
| 1. Kojic acid glucoside | 7.00 |
| 2. 4-tert-Butyl-4'-methoxy-dibenzoylmethane | 2.00 |
| 3. 2-Ethylhexyl p-methoxycinnamate | 0.05 |
| 4. Ethylene glycol monostearate | 3.00 |
| 5. Polyoxyethylene cetyl ether (60E.O.) | 5.00 |
| 6. Ginseng extract | 2.00 |
| 7. Japanese chirate extract | 0.50 |
| 8. p-hydroxybenzoic acid ester | 0.10 |
| 10. Sodium citrate | 0.30 |
| 11. 5% Solution of elastin hydrolyzate | 4.00 |
| 12. Disodium edetate | 0.01 |
| 13. Purified water to make | 100.00 |

Formulation example 6 [Cream pack]

| | (% by weight) |
|---|---|
| 1. Ethyl kojate | 2.00 |
| 2. 4-tert-butyl-4'-methoxy-dibenzoylmethane | 0.50 |
| 3. Trimethylolpropane trioctanoate | 2.00 |
| 4. Oleic acid glyceride | 5.00 |
| 5. Stearic acid diethanolamide | 5.00 |
| 6. Stearic acid | 5.00 |
| 7. Myristic acid | 0.50 |
| 8. Coconut oil | 15.00 |
| 9. Natural vitamin E | 0.04 |
| 10. p-Hydroxybenzoic acid ester | 0.20 |

-continued

| | (% by weight) |
|---|---|
| 11. Solution of sodium dl-pyrrolidonecarboxylate | 5.00 |
| 12. Disodium edetate | 0.01 |
| 13. Purified water to make | 100.00 |

Formulation example 7 [Ointment]

| | (% by weight) |
|---|---|
| 1. Kojic acid | 1.00 |
| 2. Oxybenzonesulfonic acid | 0.10 |
| 3. Phenyl salicylate | 0.40 |
| 4. Sodium hydroxymethoxy-benzophenonesulfonate | 1.00 |
| 5. Sorbitol sesquiisostearate | 2.00 |
| 6. Coconut oil faty acid monoethanolamide | 5.00 |
| 7. Vaseline | 10.00 |
| 8. Stearic acid | 5.00 |
| 9. Oleic acid | 1.00 |
| 10. Olive oil | 10.00 |
| 11. p-Hydroxybenzoic acid ester | 0.20 |
| 12. Carrageenan | 5.00 |
| 13. Disodium edetate | 0.01 |
| 14. Purified water to make | 100.00 |
| 14. Purified water to make | 100.00 |

Formulation example 8 [Cataplasm]

| | (% by weight) |
|---|---|
| 1. Kojic acid fructoside | 0.50 |
| 2. Glyceryl p-aminobenzoate | 4.00 |
| 3. Hexyldecyl dimethyloctanoate | 1.00 |
| 4. Stearic acid diethanolamide | 3.00 |
| 5. Polyacrylic acid | 27.00 |
| 6. Licorice extract (ethanol extract) | 0.10 |
| 7. Scutellaria root extract (aqueous extract) | 0.05 |
| 8. Disodium edetate | 0.05 |
| 9. Sodium polyacrylate | 7.00 |
| 10. Aluminum chloride | 0.30 |
| 11. Conc. glycerin | 20.00 |
| 12. Titanium oxide | 4.00 |
| 13. Purified water to make | 100.00 |

Formulation example 9 [Essence]

| | (% by weight) |
|---|---|
| 1. Kojic acid | 1.00 |
| 2. Urocanic acid | 0.50 |
| 3. 2-Ethylhexyl p-methoxycinnamate | 1.00 |
| 4. Polyoxyl 40 stearate | 0.50 |
| 5. Octyldodecyl myristate | 1.50 |
| 6. Coconut oil fatty acid monoethanolamide | 2.00 |
| 7. Stearic acid | 0.50 |
| 8. Linolenic acid | 0.50 |
| 9. Avocado oil | 2.00 |
| 10. Turtle oil | 3.00 |
| 11. Natural vitamine E | 0.04 |
| 12. p-Hydroxybenzoic acid ester | 0.20 |
| 13. 1% Aqueous solution of carboxyvinyl polymer | 5.00 |
| 14. Xanthane gum | 0.14 |
| 15. Disodium edetate | 0.01 |
| 16. Purified water to make | 100.00 |

It has been confirmed that the above-described Formulation Examples 1 to 9 provide preparations having the same satisfactory results as are shown in Tables 1 and 2.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the clams are therefore intended to be embraned therein.

What is claimed is:

1. A method of preventing an ultraviolet light absorbent from separating and kojic acid or a derivative thereof from being discolored or decomposed in a preparation comprising a nonionic surfactant as its base; 0.1 to 5% by weight of kojic acid or a derivative thereof; and 0.1 to 10% by weight of an ultraviolet light absorbent; which comprises adding to the preparation at least 0.1 to 10% by weight of at least one fatty acid ester selected from the group consisting of fatty acid esters consisting of an alcohol having 3 to 18 carbon atoms and a fatty acid having 3 to 22 carbon atoms, fatty acid esters consisting of ethylene, propylene or polyethylene glycol and a fatty acid having 8 to 18 carbon atoms, fatty acid esters consisting of trimethylolpropane or pentaerythritol and a fatty acid having 8 to 14 carbon atoms, fatty acid esters consisting of sorbitol or sucrose and a fatty acid having 8 to 18 carbon atoms, fatty acid esters consisting of glycerol or a polyglycerol and a fatty acid having 6 to 20 carbon atoms, and fatty acid esters consisting of a polyoxyethylene glycerol and a fatty acid having 18 carbon atoms.

* * * * *